United States Patent
O'Heeron et al.

(10) Patent No.: US 12,133,870 B2
(45) Date of Patent: Nov. 5, 2024

(54) TREATMENT OF OPIOID ADDICTION USING FIBROBLASTS AND PRODUCTS THEREOF

(71) Applicant: SPINALCYTE LLC, Houston, TX (US)

(72) Inventors: Pete O'Heeron, Houston, TX (US); Thomas Ichim, San Diego, CA (US)

(73) Assignee: SPINALCYTE LLC, Houston, TX (US)

( * ) Notice: Subject to any disclaimer, the term of this patent is extended or adjusted under 35 U.S.C. 154(b) by 689 days.

(21) Appl. No.: 16/822,746

(22) Filed: Mar. 18, 2020

(65) Prior Publication Data

US 2020/0297773 A1 Sep. 24, 2020

Related U.S. Application Data

(60) Provisional application No. 62/820,721, filed on Mar. 19, 2019.

(51) Int. Cl.
*A61K 35/33* (2015.01)
*C12N 5/077* (2010.01)

(52) U.S. Cl.
CPC ............ *A61K 35/33* (2013.01); *C12N 5/0656* (2013.01); *C12N 2501/113* (2013.01); *C12N 2501/115* (2013.01); *C12N 2501/15* (2013.01)

(58) Field of Classification Search
CPC .... A61K 35/33; A61K 31/13; A61K 2300/00; A61K 31/4745; A61K 31/485; C12N 5/0656; A61P 25/36
See application file for complete search history.

(56) References Cited

U.S. PATENT DOCUMENTS

2008/0187521 A1 8/2008 Xue et al.
2010/0119490 A1 5/2010 Yoon et al.
2017/0258843 A1 9/2017 Ichim et al.

FOREIGN PATENT DOCUMENTS

WO WO 2005/056777 6/2005
WO WO 2018/169094 9/2018

OTHER PUBLICATIONS

Ezquer et al., Intravenous administration of anti-inflammatory mesenchymal stem cell spheroids reduces chronic alcohol intake and abolishes binge-drinking. Sci Rep 8, 4325 (2018). (Year: 2018).*
Ichim et al., Fibroblasts as a practical alternative to mesenchymal stem cells. J Transl Med 16, 212 (2018). (Year: 2018).*
Oses et la., Preconditioning of adipose tissue-mesenchymal stem cells deferoxamine increases the production of pro-angiogenic neuroprotective and anti-inflammatory factors: Potential application in the treatment of diabetic neuropathy. PloS One 12, e0178011 (2017). (Year: 2017).*
Haniffa et al., (2007) Adult human fibroblasts are potent immunoregulatory cells and functionally equivalent to mesenchymal stem cells, The Journal of Immunology, 179(3) pp. 1595-1604 (Year: 2007).*
Soundararajan et al., (2018) Fibroblasts and mesenchymal stem cells: Two sides of the same coin? Journal of Cellular Physiology 233(12) pp. 9099-9109. (Year: 2018).*
Ichim et al.: "Fibroblasts as a Practical Alternative to Mesenchymal Stern Cells", Journal of Translational Medicine, Jul. 27, 2018; vol. 16, No. 212; pp. 1-9.
Rafaiee, R et al.: "Bone Marrow Derived Mesenchymal Stem Cells In Addiction Related Hippocampal Damages", International Journal of Molecular and Cellular Medicine. Jun. 20, 2018; vol. 7, No. 2; pp. 69-79.
Denu et al., "Fibroblasts and Mesenchymal Stromal/Stem Cells Are Phenotypically Indistinguishable," Acta Haematologica, 136(2):85-97, 2016.
Extended European Search Report issued in European Patent Application No. 20774671.0, dated Nov. 10, 2022.
Office Communication issued in European Patent Application No. 20774671.0, dated Oct. 12, 2023.
Wong et al., "Therapeutic transdifferentiation of human fibroblasts into endothelial cells using forced expression of lineage-specific transcription factors," J Tissue Eng., 7:1-10, Jan. 2016.
Zhang et al., "The multi-differentiation potential of peripheral blood mononuclear cells," Stem Cell Res Ther., 3(6):48, 10 pages, Nov. 2012.
Balducci et al., "Chapter 13. The difference between mesenchymal stromal cells and fibroblasts." In: The Biology and Therapeutic Application of Mesenchymal Cells. Kerry Atkinson, Ed., John Wiley & Sons, Inc., pp. 441-455, 2017.
Colantoni et al., "Opioids Induce Apoptosis: Experimental Evidence and Considerations," Pharmacologyonline, 3:90-98, 2006.
English translation of Office Communication issued in Japanese Patent Application No. 2021-556511, dated Jan. 20, 2024.
Even-Chen and Barak, "The role of fibroblast growth factor 2 in drug addiction," European Journal of Neuroscience, pp. 1-10, 2018.

\* cited by examiner

*Primary Examiner* — Kara D Johnson
(74) *Attorney, Agent, or Firm* — Norton Rose Fulbright US LLP

(57) ABSTRACT

Disclosed are methods and compositions comprising fibroblasts and/or products derived thereof for the inhibition and/or treatment of addiction of any kind, such as opioid addiction. In some embodiments, methods comprise treating a patient addicted to opioids by administering a fibroblast population at a concentration sufficient for suppression of addiction-associated brain damage. In some embodiments, the fibroblasts express CD31 and/or CD73 markers. In some embodiments, fibroblasts are used to endow neuronal regeneration in order to overcome changes in the brain associated with addiction. Some embodiments relate to the stimulation of hippocampal regeneration subsequent to addiction induced damage.

31 Claims, No Drawings

TREATMENT OF OPIOID ADDICTION USING FIBROBLASTS AND PRODUCTS THEREOF

This application claims priority to U.S. Provisional Patent Application Ser. No. 62/820,721, filed Mar. 19, 2019, which is incorporated by reference herein in its entirety.

TECHNICAL FIELD

The present disclosure relates generally to embodiments of cell biology and medicine. In particular embodiments the disclosure concerns regenerative medicine for the treatment of addiction. More particularly, the current disclosure pertains to compositions and methods comprising fibroblasts or products derived thereof for the treatment of opioid addiction.

BACKGROUND

Dependence on opioids, in the form of heroin or prescription pain medications, for example, is a significant health concern. It is known that during the period of 1999-2015, 568,699 persons died from drug overdoses in the United States. Drug overdose deaths in the United States increased 11.4% from 2014 to 2015 resulting in 52,404 deaths in 2015, including 33,091 (63.1%) that involved an opioid. The largest rate increases from 2014 to 2015 occurred among deaths involving synthetic opioids other than methadone (72.2%). Because of demographic and geographic variations in overdose deaths involving different drugs, The Center for Disease Control (CDC) examined age-adjusted death rates for overdoses involving all opioids, opioid subcategories (i.e., prescription opioids, heroin, and synthetic opioids), cocaine, and psychostimulants with abuse potential (psychostimulants) by demographics, urbanization levels, and in 31 states and the District of Columbia (DC). There were 63,632 drug overdose deaths in 2016; 42,249 (66.4%) involved an opioid. From 2015 to 2016, deaths increased across all drug categories examined. The largest overall rate increases occurred among deaths involving cocaine (52.4%) and synthetic opioids (100%), likely driven by illicitly manufactured fentanyl (IMF). Increases were observed across demographics, urbanization levels, and states and DC [1]. It is generally accepted that the authors concluded that the opioid overdose epidemic in the United States continues to worsen [2-4].

Methadone maintenance treatment for opioid dependence reduces morbidity, mortality, and the spread of infectious diseases but is restricted to licensed specialty clinics in the United States, requires frequent clinic visits, and has a high risk of overdose [5].

These issues have led to increased use of buprenorphine as a treatment for opioid addiction, and numerous studies support the efficacy of sublingually administered buprenorphine. In the United States, buprenorphine can be prescribed in office-based physician practice. However, there are several concerns about diversion and nonmedical use of sublingual buprenorphine. Poor treatment adherence, resulting in craving and withdrawal symptoms that increase the likelihood of relapse, is also a concern with sublingual buprenorphine [6, 7].

Generally speaking, addiction is defined as a chronic disease with obligation to take drugs and/or alcohol, no control on restraining intake, and having negative emotional feeling during withdrawal period. Addiction does not just affect the addict's life, but also it has a huge burden on the society and economy. It was revealed that addictive agents have a great anatomical and physiological impact on the brain centers, resulting in psychological, behavioral, and sensory-motor changes. It was demonstrated that addictive substances affect dopaminergic pathways that connect the ventral tegmental area to the prefrontal cortex via limbic system in particular in the nucleus accumbens, amygdala, ventral pallidum, and hippocampus [8].

Currently, there is a need for safe therapeutic compositions and methods and regimens that properly treat and/or help manage opioid addiction.

BRIEF SUMMARY OF THE DISCLOSURE

Embodiments of the disclosure encompass methods and compositions related to treatment or prevention of addiction or substance abuse of any kind. In particular embodiments, the disclosure concerns administration of fibroblasts and/or products derived thereof that are employed to inhibit, and/or treat addiction, such as opioid addiction. The current embodiments include, inter alia, compositions and methods relating to treating addiction and substance abuse. In some embodiments, the compositions and methods relate to treating or inhibiting addiction or substance abuse by the administration of fibroblasts and/or products derived thereof. In some embodiments, the fibroblasts express CD31 and/or CD73 with or without other markers. In some embodiments, a patient addicted to a substance is administered a fibroblast population at a concentration sufficient for suppression of addiction and/or associated brain damage. In some embodiments, fibroblasts are used to endow neuronal regeneration in order to overcome changes in the brain associated with addiction. In some embodiments, methods pertain to stimulating hippocampal regeneration after addiction-induced damage. The disclosure also provides for the use of fibroblasts as a cellular therapy for reversion of addictive states.

Here, embodiments include, compositions and formulations comprising fibroblasts for treating opioid addiction, treating opioid use disorder, treating opioid withdrawal symptoms, reversing an addictive state, inhibiting opioid addiction, preventing or treating or ameliorating opioid addiction, preventing opioid withdrawal symptoms, reducing the severity or duration of opioid addiction, preventing relapse of opioid addiction, decreasing the potential for opioid tolerance, decreasing physical dependence, preventing opioid abuse or overcoming addiction-associated hippocampal damage, administering fibroblast to correct addition-associated alterations of the hippocampal function, selecting fibroblasts for enhanced efficacy for treating opioid addiction, for treating any addiction, endowing neuronal regeneration, stimulating hippocampal regeneration, inhibiting neuro-inflammation, enhancing renewal of neuronal progenitor cells, inhibiting excitotoxicity, preventing apoptosis of brain cells or any combination thereof.

Certain aspects of the disclosure relate to methods of treating opioid addiction, treating opioid use disorder, treating opioid withdrawal symptoms, reversing an addictive state, using fibroblasts for preventing or treating or ameliorating opioid addiction, inhibiting opioid addiction, preventing opioid withdrawal symptoms, reducing the severity or duration of opioid addiction, preventing relapse of opioid addiction, decreasing the potential for opioid tolerance, decreasing physical dependence, preventing opioid abuse, overcoming addiction-associated hippocampal damage or administering fibroblast to correct addition-associated alterations of the hippocampal function, selecting fibroblasts for enhanced efficacy for treating opioid addiction, using fibroblast for treating any addiction, endowing neuronal regeneration, stimulating hippocampal regeneration, inhibiting neuro-inflammation, enhancing renewal of neuronal progenitor cells, inhibiting excitotoxicity, preventing apoptosis of brain cells or any combination thereof.

Embodiments of these methods are disclosed throughout the disclosure. Any embodiment of one method can be implemented in the context of another embodiment discussed herein. Similarly any method herein can exclude one or more steps described herein. In some aspects, any one of the methods disclosed herein can involve the following steps: diagnosing, treating, ameliorating, inhibiting, and concentrating.

Further aspects of the disclosure relates to a method of treating addiction in a subject, the method comprising administering to the subject a composition comprising a fibroblast cell, a plurality thereof or a product derived thereof, wherein said cell expresses CD31 and/or CD73 markers. In some embodiments the cell is generated by a method comprising the steps of: a) obtaining fibroblasts; b) culturing said fibroblasts; c) obtaining a single cell suspension; and d) extracting from said single cell suspension fibroblast cells expressing markers CD31 and CD73. In some embodiments, the fibroblast cell or plurality thereof further expresses CD45 and/or CD34 markers.

In some embodiments, the product derived thereof comprises a supernatant from a fibroblast cell culture. In some embodiments, the supernatant from a fibroblast cell culture comprises at least one trophic factor. The trophic factor can be a hormone, cytokine, extracellular matrix, protein, vesicle, antibody, or granules.

In some embodiments, the methods of the current disclosure further comprise a step of optionally priming said fibroblast cells expressing markers CD31 and/or CD73 with an agent capable of augmenting production of neuronal regenerative properties of said cells. As used herein, the term "augmenting production of neuronal regenerative properties of said cells" refers to culturing with one or more agents that endow the fibroblasts with an enhanced ability to promote neural progenitors to multiply, as well as protect existing neural progenitors from apoptosis (see below). For example, one can culture fibroblasts in aFGF that will allow the fibroblasts to possess enhanced neuronal regenerative properties. In specific cases, the methods of the current disclosure further comprise a step of optionally priming the fibroblast cells expressing markers CD31 and/or CD73 with one or more agents capable of "promoting neuronal regeneration."

In some embodiments of the methods or compositions of the current disclosure, culturing said fibroblasts is in a medium that allows proliferation of said fibroblasts. In some embodiments, culturing of said fibroblast cell or plurality thereof produces activin A, adrenomedullin, aFGF, ALK1, ALK5, ANF, angiogenin, angiopoietin-1, angiopoietin-2, angiopoietin-3, angiopoietin-4, bFGF, B61, bFGF inducing activity, cadherins, CAM-RF, cGMP analogs, ChDI, CLAF, claudins, collagen, collagen receptors alpha$_1$beta$_1$ and alpha$_2$beta$_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shpingolipid G-protein coupled receptor-1 (EDG1), ephrins, Epo, HGF, TGF-beta, PD-ECGF, PDGF, IGF, IL8, growth hormone, fibrin fragment E, FGF-5, fibronectin and fibronectin receptor .alpha.5.beta. 1, Factor X, HB-EGF, HBNF, HGF, HUAF, heart derived inhibitor of vascular cell proliferation, Ill, IGF-2 IFN-gamma, integrin receptors, K-FGF, LIF, leiomyoma-derived growth factor, MCP-1, macrophage-derived growth factor, monocyte-derived growth factor, MD-ECI, MECIF, MMP 2, MMP3, MMP9, urokinase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-beta, PD-ECGF, PAI-2, PD-ECGF, PF4, P1GF, PKR1, PKR2, PPAR-gamma, PPAR-gamma ligands, phosphodiesterase, prolactin, prostacyclin, protein S, smooth muscle cell-derived growth factor, smooth muscle cell-derived migration factor, sphingosine-1-phosphate-1 (SIP1), Syk, SLP76, tachykinins, Tie 1, Tie2, TGF-beta, and TGF-beta receptors, TIMPs, TNF-alpha, transferrin, thrombospondin, urokinase, VEGF-A, VEGF-B, VEGF-C, VEGF-D, VEGF-E, VEGF, VEGF.sub.164, VEGI, EG-VEGF or any combination thereof. In some embodiments, the fibroblast cell is cultured in a growth medium, in a conditioned medium or in a reprogramming medium.

In some embodiments, the neuronal regenerative properties include inhibiting neuro-inflammation, enhancing renewal of neuronal progenitor cells, inhibiting excitotoxicity, preventing or inhibiting apoptosis of brain cells or any combination thereof. In some embodiments, the neuronal regeneration is regeneration of the hippocampus. In some embodiments, the neuronal progenitor cells are cells resident in the dentate gyrus. In some embodiments, the neuronal progenitor cells are cells resident in the subventricular zone. In some embodiments, the neuro-inflammation is mediated by inflammatory cytokine TNF-alpha or cytokine IL-1, cytokine IL-6.

In some embodiments, preventing or inhibiting apoptosis is by production of IGF-1 or VEGF.

In some embodiments, the methods further include activating said fibroblasts by exposure to one or more toll like receptor agonists. The toll like receptor may be TLR-1 or TLR-2 or TLR-3 or TLR-4 or TLR-5 or TLR-6 or TLR-7 or TLR-8 or TLR-9 or a combination thereof.

In some embodiments, the agonist of TLR-1 is Pam3CSK4.

In some embodiments, the agonist of agonist of TLR-2 is HKLM.

In some embodiments, the agonist of TLR-3 is Poly:IC.

In some embodiments, the agonist of TLR-4 is LPS, buprenorphine, carbamazepine, fentanyl, levorphanol, Methadone, cocaine, morphine, oxacarbazepine, oxycodone, pethidine, glucuronoxylomannan from *Cryptococcus*, morphine-3-glucuronide, lipoteichoic acid, β-defensin 2, is small molecular weight hyaluronic acid, fibronectin EDA, snapin, tenascin C.

In some embodiments, the agonist of TLR-5 is flagellin.

In some embodiments, the agonist of TLR-6 is FSL-1.

In some embodiments, the agonist of TLR-7 is imiquimod.

In some embodiments, the agonist of TLR8 is ssRNA40/LyoVec.

In some embodiments, the agonist of TLR-9 is a CpG oligonucleotide, ODN2006, or agatolimod.

In some embodiments, the addiction is an opioid addiction, such as an addiction of heroin, OxyContin, or vicodin. The opioid may or may not be a prescription opioid. The opioid may be natural opiates that are alkaloids, including nitrogen-containing base chemical compounds that occur in plants such as the opium poppy. Natural opiates include morphine, codeine, and thebaine. The opioid may be semi-synthetic/manmade opioids that are created in labs from natural opiates. Semi-synthetic opioids include hydromorphone, hydrocodone, and oxycodone (the prescription drug OxyContin), as well as heroin, which is made from morphine. The opioid may be fully synthetic/manmade opioids that are completely manmade, including fentanyl, pethidine, levorphanol, methadone, tramadol, and dextropropoxyphene. In some embodiments, the addiction is an heroin addiction.

In some embodiments of the methods or compositions of the current disclosure, the fibroblast cell is autologous or allogenic or xenogenic with respect to an individual being treated with the fibroblast cell.

In some embodiments of the methods or compositions of the current disclosure, the subject is also administered memantine. Memantine can be administered concurrently or before or after the administration of a fibroblast cells. It can be administered in various dosages including but not limited to 5-100 mg/day or 10-30 mg/day. In some embodiments, the subject is also administered an analgesic, Naloxone or Acompatase or others.

In some embodiments of the methods of the current disclosure, the fibroblast cell or plurality thereof is encapsulated. In some embodiments it is encapsulated by a membrane, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, or polyethersulfone (PES) hollow fibers.

Further embodiments of the current disclosure relate to a method of treating brain damage associated with opioid addiction comprising administration of a therapeutic cell, wherein said therapeutic cell is generated by the steps of: a) obtaining fibroblasts; b) culturing said fibroblasts in a liquid media capable of allowing for proliferation of said fibroblasts; c) extracting from single cell suspension cells expressing the markers CD31 and/or CD73; and d) optionally priming said cells with an agent capable of augmenting production of neuronal regenerative properties of said cells.

Further embodiments of the current disclosure relate to a method of treating associated hippocampal damage in a subject comprising administering to the subject a fibroblast cell or an activated fibroblast cell expressing CD31 and/or CD73 markers by placing said fibroblast cell in the subgranular zone (SGZ) of said subject.

Further embodiments of the current disclosure relate to a method treating addiction in a subject comprising, obtaining fibroblasts; culturing said fibroblasts in a medium that allows proliferation of said fibroblasts; extracting from single cell suspension cells; isolating fibroblast cells that express markers CD31 and/or CD73; and administrating to the subject a composition comprising a fibroblast cell, wherein said cell expresses CD31 and/or CD73 markers.

Further embodiments of the current disclosure relate to a method of treating opioid addiction-associated brain damage in a subject comprising administrating to the subject a fibroblast cell, wherein said cell expresses CD31 and/or CD73 markers. In some embodiments, the cell was generated by a method comprising the steps of: a) obtaining fibroblasts; b) culturing said fibroblasts in a medium that allows proliferation of said fibroblasts; c) extracting from single cell suspension cells; and d) isolating fibroblast cells that express markers CD31 and/or CD73. In some embodiments, the cell is generated by the steps of: a) obtaining fibroblasts; b) culturing said fibroblasts in a liquid media capable of allowing for proliferation of said fibroblasts; c) extracting from said single cell suspension cells expressing the markers CD31 and/or CD73; and d) optionally priming said cells with an agent capable of augmenting production of neuronal regenerative properties of said cells. The neuronal regenerative properties can be a) inhibiting neuro-inflammation; b) enhancing renewal of neuronal progenitor cells; c) inhibiting excitotoxicity; or d) preventing apoptosis of brain cells.

Further embodiments of the current disclosure relate to a pharmaceutical composition for the treatment of addiction, comprising a fibroblast cell or plurality thereof expressing CD31 and/or CD73. The cell can be generated by the steps of: a) obtaining fibroblasts; b) culturing said fibroblasts in a liquid media capable of allowing for proliferation of said fibroblasts; c) extracting from said single cell suspension cells expressing the markers CD31 and/or CD73; and d) optionally priming said cells with an agent capable of augmenting production of neuronal regenerative properties of said cells.

It is contemplated that any method or composition described herein can be implemented with respect to any other method or composition described herein and that different embodiments may be combined.

Use of the one or more compositions may be employed based on any of the methods described herein. Other embodiments are discussed throughout this disclosure. Any embodiment discussed with respect to one aspect of the disclosure applies to other aspects of the disclosure as well and vice versa. The embodiments in the Example section are understood to be embodiments that are applicable to all aspects of the technology described herein.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying FIGURES. It is to be expressly understood, however, that each of the FIGURES is provided for the purpose of illustration and description only and is not intended as a definition of the limits of the present disclosure.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE DISCLOSURE

Disclosed are methods and compositions comprising fibroblasts and/or products derived thereof for the inhibition and/or treatment of addiction such as opioid addiction. In one embodiment, a patient addicted to opioids is administered a fibroblast population at a concentration sufficient for suppression of addiction-associated brain damage. In one embodiment of the invention, fibroblasts are used to endow neuronal regeneration in order to overcome changes in the brain associated with addiction. Some embodiments relate to the stimulation of hippocampal regeneration subsequent to addiction induced damage.

In particular embodiments there are methods that include administration of fibroblasts and/or products derived thereof that can be employed to inhibit, and/or treat addiction such as opioid addiction. The current embodiments include, inter alia, compositions and methods relating to treating addiction and substance abuse. In some embodiments, the compositions and methods relate to treating or inhibiting opioid addiction by the administration of fibroblasts and/or products derived thereof. In some embodiments, a patient addicted to opioids is administered a fibroblast population at a concentration sufficient for suppression of addiction and/or associated brain damage. In some embodiments, fibroblasts are used to endow neuronal regeneration in order to overcome changes in the brain associated with addiction. In some embodiments, methods pertain to stimulating hippocampal regeneration after addiction-induced damage. The disclosure also provides for the use of fibroblasts as a cellular therapy for reversion of addictive states. The fibroblasts (therapeutic cells) can be autologous, allogenic or xenogenic.

The meaning of terms as intended is defined herein below.

I. Definitions

"Opioid addiction" or "Opioid Use Disorder" refers to a condition characterized by the harmful consequences of repeated opioid use, a pattern of compulsive opioid use, and sometimes physiological dependence on opioid including tolerance and/or symptoms of withdrawal.

"Drug withdrawal" refers to a group of symptoms that occur upon the abrupt discontinuation or sudden decrease in intake of medications or recreational drugs. Consequently, "opioid withdrawal" refers to the group of symptoms that occur upon the dramatic reduction, abrupt discontinuation or decrease in intake of opioids or opiates. Withdrawal symptoms may also start between doses. Withdrawal symptoms from opioids include but are not limited to anxiety, depression, sweating, vomiting, and diarrhea, muscle cramping, agitation, insomnia, yawning dilated pupils, goose bumps, abdominal cramping, runny nose and increased tearing, for example.

The term "substantially the same" or "not significantly different" refers to a level of expression that is not significantly different than what it is compared to. Alternatively, or in conjunction, the term substantially the same refers to a level of expression that is less than 2, 1.5, or 1.25 fold different than the expression or activity level it is compared to.

A "subject," "individual" or "patient" is used interchangeably herein and refers to a vertebrate, for example a primate, a mammal or a human. Mammals include, but are not limited to equines, canines, bovines, ovines, murines, rats, simians, humans, farm animals, sport animals and pets. Also intended to be included as a subject are any subjects involved in clinical research trials not showing any clinical sign of disease, or subjects involved in epidemiological studies, or subjects used as controls.

"Diagnosis" may refer to the process of attempting to determine or identify a possible disease or disorder, or to the opinion reached by this process. From the point of view of statistics the diagnostic procedure may involve classification tests.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that a numerical value discussed herein may be used with the term "about" or "approximately." The term "about" or "around" is also used to indicate that a value includes the standard deviation of error for the device or method being employed to determine the value.

As used herein, the term "comprising" is intended to mean that the compositions and methods include the recited elements, but not excluding others. "Consisting essentially of" when used to define compositions and methods, shall mean excluding other elements of any essential significance to the combination for the stated purpose. "Consisting essentially of" in the context of pharmaceutical compositions of the disclosure is intended to include all the recited active agents and excludes any additional non-recited active agents, but does not exclude other components of the composition that are not active ingredients. Thus, a composition consisting essentially of the elements as defined herein would not exclude trace contaminants from the isolation and purification method and pharmaceutically acceptable carriers, such as phosphate buffered saline, preservatives and the like. "Consisting of" shall mean excluding more than trace elements of other ingredients and substantial method steps for administering the compositions of this invention or process steps to produce a composition or achieve an intended result. Embodiments defined by each of these transition terms are within the scope of this invention. It is contemplated that embodiments described in the context of the term "comprising" may also be implemented in to context of the term "consisting of" or "consisting essentially of."

The terms "protein", "polypeptide" and "peptide" are used interchangeably herein when referring to a gene product or functional protein.

The terms "ameliorating," "inhibiting," or "reducing," or any variation of these terms, when used in the claims and/or the specification includes any measurable decrease or complete inhibition to achieve a desired result.

The term "inhibitor" refers to a therapeutic agent that indirectly or directly inhibits the activity or expression of a protein, process (e.g. metabolic process), or biochemical pathway The term "agonist" describes a moiety or agent that interacts with and activates a receptor such as a G-protein-coupled receptor, for instance an opioid receptor, and can thereby initiate a physiological or pharmacological response characteristic of that receptor.

As used herein, a "partial agonist" is moiety, or agent, that binds to and activates a given receptor, but have only partial efficacy at the receptor relative to a full agonist.

As used herein an "antagonist" describes a moiety that competitively binds to the receptor at the same site as an agonist, but does not activate the intracellular response initiated by the active form of the receptor and can thereby inhibit the intracellular responses by an agonist or partial agonist.

The term "pharmaceutical formulation" is intended to mean a composition or a mixture of compositions comprising at least one active ingredient; including but not limited to, salts, solvates, and hydrates of compounds described herein.

As used herein, "treating," "treatment" or "therapy" is an approach for obtaining beneficial or desired clinical results. This includes the reduction or the alleviation of symptoms, the reduction or alleviation of pain, or the reduction in the frequency of withdrawal symptoms, and/or reduction in the occurrence of anxiety or depression and/or reduction in suicidal thinking. Furthermore, these terms are intended to encompass curing as well as ameliorating at least one symptom of the condition or disease. For example, in the case of opioid use disorders, a response to treatment includes the cessation in the use of opioids, or the cessation of at least one opioid withdrawal symptom.

The term "therapeutically effective amount" refers to an amount of cells that treats or inhibits addiction, or withdrawal symptoms in the subject. In some embodiments, the therapeutically effective amount inhibits at least or at most or exactly 100, 99, 98, 96, 94, 92, 90, 85, 80, 75, 70, 65, 60, 55, 50, 40, 30, 20, or 10%, or any derivable range therein, of a symptom expression.

The term "administered" or "administering", as used herein, refers to any method of providing a composition to an individual such that the composition has its intended effect on the patient. For example, one method of administering is by an indirect mechanism using a medical device such as, but not limited to a catheter, applicator gun, syringe etc. A second exemplary method of administering is by a direct mechanism such as, local tissue administration, etc.

As used herein, "allogeneic" refers to tissues or cells from another body that in a natural setting are immunologically incompatible or capable of being immunologically incompatible, although from one or more individuals of the same species.

As used herein, the term "allotransplantation" refers to the transplantation of organs, tissues, and/or cells from a donor to a recipient, where the donor and recipient are different individuals, but of the same species. Cells or tissue transplanted by such procedures is referred to as an allograft or allotransplant.

As used herein, "autologous" refers to tissues or cells that are derived or transferred from the same individual's body (i.e., autologous blood donation; an autologous bone marrow transplant).

As used herein, the term "autotransplantation" refers to the transplantation of organs, tissues, and/or cells from one part of the body in an individual to another part in the same individual, i.e., the donor and recipient are the same individual. Tissue transplanted by such "autologous" procedures is referred to as an autograft or autotransplant.

The term "biologically active" refers to any molecule having structural, regulatory or biochemical functions. For example, biological activity may be determined, for example, by restoration of wild-type growth in cells lacking protein activity. Cells lacking protein activity may be produced by many methods (i.e., for example, point mutation and frame-shift mutation). Complementation is achieved by transfecting cells that lack protein activity with an expression vector that expresses the protein, a derivative thereof, or a portion thereof. In other cases, a fragment of a gene product (such as a protein) may be considered biologically active (or it may be referred to as functionally active) if it retains the activity of the full-length gene product, although it may be at a reduced but detectable level of the activity of the full-length gene product.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more. It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Furthermore, an embodiment discussed in the Examples may be applied in the context of any other embodiments discussed herein.

The use of the word "a" or "an" when used in conjunction with the term "comprising" in the claims and/or the specification may mean "one," but it is also consistent with the meaning of "one or more," "at least one," and "one or more than one."

II. Various Embodiments

Embodiments of the disclosure concern the treatment or prevention of addiction or substance abuse of any kind, including drugs, narcotics, alcohol, marijuana, hallucinogens (including mushrooms, PCP, LSD, etc.), inhalants (such as paint thinner or glue), sedatives, hypnotics, anxiolytics, tranquilizers, cocaine, methamphetamine, stimulants of any kind, tobacco, sex, gambling, or a combination thereof.

In one embodiment, fibroblasts, including those with regenerative properties, are used (in some cases, to provide chemical and nanoparticle support) in order to assist the nervous system in overcoming addiction or substance abuse of any kind. In the art it is known that a major characteristic of addiction is the proclivity for recidivism after a period of abstinence. Dopamine (DA) transmission in the nucleus accumbens (NA) is involved in the reward process. DA receptor agonists are self-administering and modulate opioid-seeking behavior while $D_1$ DA antagonists in the NA reduces the reinforcing efficacy of opioids. Glutamate transmission in the NA is associated with a behavioral sensitization while AMPA receptor inhibition prevents both the expression of sensitization and increased glutamate transmission following opioid administration in sensitized rats. Behavioral sensitization to psychomotor stimulants correlates with abnormalities in the mesoaccumbens dopamine (DA) system. These include at least DA autoreceptor subsensitivity in the ventral tegmental area and $D_1$ receptor supersensitivity in the nucleus accumbens (NA).

From animal studies, both NMDA antagonists (non-competitive and competitive) and AMPA antagonists prevented both opioid sensitization and receptor alterations. Glutamate transmission from the medial prefrontal cortex to the mesoaccumbens DA system was critical for the induction of opioid sensitization and receptor correlations. Glycine binding site NMDA antagonists and inhibitors of nitric oxide synthetase (NOS) have been reported to attenuate the development of morphine tolerance and even reverse established tolerance or dependence. The modulation of tolerance and dependence by glutamate antagonists without effecting the analgesic effect of morphine suggests prevention of neuronal plasticity associated with the adaptive changes mediated by the NMDA/NO cascade. Within neurons expressing both the NMDA and mu opioid receptor, the magnitude of NMDA receptor-mediated inward current is enhanced by mu opioid agonists. Mu receptor activation may function by removing the Mg++ block, allowing increased NMDA activation and the subsequent formation of NO. This cascade alters gene expression and produces neuronal plasticity, resulting in both tolerance and dependence. The latter neurochemical events decrease the analgesia cascade effect of morphine. Thus N-methyl-D-aspartate (NMDA) antagonists can interfere with the phenomena of drug tolerance without having a direct effect on the analgesic effect of mu opioid stimulation.

In one embodiment the disclosure encompasses the use of fibroblasts as a therapeutic cellular source for reducing dependency, in part by modulating NMDA transmission. The symptoms of drug tolerance, dependency, addiction and withdrawal that occur in both opioid addicts and chronic pain patients may be partially mediated by the NMDA receptor complex. In animal studies, a glycine-site receptor antagonist revealed efficacy in decreasing withdrawal symptoms and eliminating opiate drug addiction. In contrast, the results of memantine in eliminating symptoms of drug withdrawal and addiction in animal studies have been conflicting and usually negative, which may reflect an inadequate treatment period. When a patient chronically addicted to heroin and cocaine was administered a glycine-site antagonist, an unexpected finding was a gradual decrease in addiction, tolerance and dependence that resulted in a drug free state for several years with no evidence of recidivism even after the drug was discontinued.

In one embodiment of the disclosure, fibroblasts are administered together with memantine to obtain synergistic effects at reducing addiction. Memantine, administered chronically in oral doses of 5-100 mg/day, advantageously 10-30 mg/day (serum levels ranging from 0.25-2.0 .mu.g/ml) is efficacious in the treatment of acute and chronic opioid tolerance. The concomitant use of memantine and analgesics in acute and chronic pain will decrease the potential of opioid tolerance and physical dependence. The administration of memantine to patients with chronic tolerance and dependence, in conjunction with current standard medical therapy (i.e., Naloxone or Acompatase) together with fibroblasts is also proposed in the treatment of illicit drug addiction. Memantine IV in patients with acute opioid or illicit overdose is also proposed. In certain embodiments, a subject is administered memantine, naloxone, acompatase or other compounds with the fibroblast compositions of the current disclosure, in an amount of about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or μg/kg or micrograms/kg/minute or mg/kg/min or micrograms/kg/hour or mg/kg/hour, or any range derivable therein.

In some embodiments, the invention teaches the administration of fibroblasts in order to overcome addiction associated hippocampal damage. It is known that the brain has the ability to produce new neural stem/progenitor cells (NSPCs) during adulthood. Hippocampus is one of the most plastic region of the brain, where granular cells in the dentate gyrus are born in adulthood. The precursors of these cells are placed in the subgranular zone (SGZ), the tissue between hilus and granule cell layer. One of the characteristic of adult-born neurons in the hippocampus is their specific electrophysiological capability for extreme changes required in early stages of maturation. This property is pivotal for formation of memories and further physiological action. The SGZ provides a proper niche for proliferation and differentiation of stem cells in dentate gyrus. In one embodiment, the administration of fibroblast cells, or activated fibroblast cells is performed in a manner capable of stimulating proliferation of SGZ cells so as to induce neuronal repair, and in some cases cause formation of memories that are not associated with the addictive memory.

In another embodiment, fibroblasts, and/or activated fibroblasts are used to modulate the environment of SGZ cells. For example, fibroblasts are administered to decrease inflammatory cytokine and inflammatory mediator production by astrocytes. It is known in the art that astrocytes as important cellular components of SGZ, play an active role in proliferation and neuronal fate commitment of NSPCs in part through release of molecular signals such as Wnt protein and sonic hedgehog (Shh). Thus in some embodiments of the disclosure, fibroblasts are administered to overcome opioid associated alteration in fibroblast activity. For example, fibroblasts have been shown to play essential roles in neural cell survival, immune responding, and modulation and metabolism of neurotransmitters. Therefore, each stimulant that can affect NSPCs or their niche in the hippocampus could make a vast modification in the memory and behavior. Bulk of studies have found the alterations in adult neurogenesis of hippocampus in neuropsycho-logical disorders such as depression, schizophrenia, bipolar disease, and addiction. Thus in one embodiment the disclosure encompasses the administration of fibroblasts to correct addiction associated alterations of hippocampal function.

In some embodiments of the disclosure, fibroblasts that are therapeutically useful for the practice of the disclosure are cultured in a manner to produce proteins/peptides wherein said proteins/peptides include but are not limited to activin A, adrenomedullin, aFGF, ALK1, ALK5, ANF, angiogenin, angiopoietin-1, angiopoietin-2, angiopoietin-3, angiopoietin-4, bFGF, B61, bFGF inducing activity, cadherins, CAM-RF, cGMP analogs, ChDI, CLAF, claudins, collagen, collagen receptors alpha$_1$beta$_1$ and alpha$_2$beta$_1$, connexins, Cox-2, ECDGF (endothelial cell-derived growth factor), ECG, ECI, EDM, EGF, EMAP, endoglin, endothelins, endostatin, endothelial cell growth inhibitor, endothelial cell-viability maintaining factor, endothelial differentiation shpingolipid G-protein coupled receptor-1 (EDG1), ephrins, Epo, HGF, TGF-beta, PD-ECGF, PDGF, IGF, IL8, growth hormone, fibrin fragment E, FGF-5, fibronectin and fibronectin receptor $alpha_5beta_1$, Factor X, HB-EGF, HBNF, HGF, HUAF, heart derived inhibitor of vascular cell proliferation, Ill, IGF-2 IFN-gamma, integrin receptors, K-FGF, LIF, leiomyoma-derived growth factor, MCP-1, macrophage-derived growth factor, monocyte-derived growth factor, MD-ECI, MECIF, MMP 2, MMP3, MMP9, urokiase plasminogen activator, neuropilin (NRP1, NRP2), neurothelin, nitric oxide donors, nitric oxide synthases (NOSs), notch, occludins, zona occludins, oncostatin M, PDGF, PDGF-B, PDGF receptors, PDGFR-beta, PD-ECGF, PAI-2, PD-ECGF, PF4, P1GF, PKR1, PKR2, PPAR-gamma, PPAR-gamma ligands, phosphodiesterase, prolactin, prostacyclin, protein S, smooth muscle cell-derived growth factor, smooth muscle cell-derived migration factor, sphingosine-1-phosphate-1 (SIP1), Syk, SLP76, tachykinins, TGF-beta, Tie 1, Tie2, TGF-.beta., and TGF-.beta. receptors, TIMPs, TNF-alpha, transferrin, thrombospondin, urokinase, VEGF-A, VEGF-B, VEGF-C, VEGF-D, VEGF-E, VEGF, VEGF.sub.164, VEGI, EG-VEGF or any combination thereof.

In the context of the present disclosure, reference to "CD45", "CD34" and "CD31" is a reference to all forms of these molecules and to functional fragments, mutants or variants thereof. In addition, reference to any isoform that may arise from alternative splicing of CD45, CD34 and CD31 mRNA or isomeric or polymorphic forms of these molecules.

Reference to "phenotypic profile" should be understood as a reference to the presence or absence of the transcription of the genes encoding the subject markers and/or the cell surface expression of the expression product translated therefrom. It should be appreciated that although most cells falling within the scope of the claimed fibroblast populations will be characterized by the presence or absence of the subject marker as a cell surface anchored expression product, some cells falling within the defined populations may initially exhibit changes only at the transcriptome level, such as when the transcription of a given marker has been upregulated but may not yet have resulted in a cell surface anchored expression product. In general, cells which progress to a new differentiative stage will transiently exhibit gene expression changes which are not yet evident in the context of changes to levels of an expression product. However, these cells nevertheless fall within the scope of the claimed cellular populations, although they will not be isolatable by the method defined herein until such time as cell surface marker expression occurs. In some embodiments of the invention fibroblasts expressing CD31 and CD73 are utilized for treatment of addiction.

Some embodiments relate to methods or means of selecting fibroblast for enhanced efficacy in treatment of opioid addiction based on expression of CD73, or lack of expression of certain proteins. Various terms are used to describe cells in culture. "Cell culture" refers generally to cells taken from a living organism and grown under controlled condition ("in culture" or "cultured"). A "primary cell culture" is a culture of cells, tissues, or organs taken directly from an organism(s) before the first subculture. Cells are expanded in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time". A "cell line" is a population of cells formed by one or more subcultivations of a primary cell culture. Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, growth conditions, and time between passaging.

A "conditioned medium" is a medium in which a specific cell or population of cells has been cultured, and then removed. When cells are cultured in a medium, they may secrete cellular factors that can provide trophic support to other cells. A trophic factor is a substance that promotes or at least supports, survival, growth, proliferation and/or maturation of a cell, or stimulates increased activity of a cell. Such trophic factors include, but are not limited to hormones, cytokines, extracellular matrix (ECM), proteins, vesicles, antibodies, and granules. The medium containing the cellular factors is the conditioned medium. In some embodiments of the current compositions or methods, a trophic factor is used. In some embodiments, the compositions and methods comprise a product derived from the fibroblasts of the current disclosure, such as for example, a supernatant from a fibroblast cell culture. it is desirable to collect supernatant from regenerative cells such as fibroblasts. Said supernatant and/or its components are utilized as a source of factors for treatment of opioid addiction. In some embodiments, fibroblasts are transfected with one or more genes to render them capable of enhanced production of factors that assist in recovery from opioid addiction (for example, interleukin-1 receptor antagonist, interleukin-10, interleukin-20, interleukin-35, interleukin-37, TGF-beta, BDNF, and/or NGF).

It is contemplated that any of the compositions or methods of the current disclosure comprise cell encapsulation. In some embodiments, cells are individually encapsulated. In some embodiments, many cells are encapsulated within the same membrane. In some embodiments in which the cells are to be removed following implantation, a relatively large size structure encapsulating many cells, such as within a single membrane, may be employed to provide a convenient means for retrieval. A wide variety of materials may be used in various embodiments for microencapsulation of stem cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Techniques for microencapsulation of cells that may be used for administration of stem cells are known to those of skill in the art and are described, for example, in Chang, P., et al., 1999; Matthew, H. W., et al., 1991; Yanagi, K., et al., 1989; Cal Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749,620; 4,814,274; 5,084,350; 5,089,272; 5,578,442; 5,639,275; and 5,676,943. All of the foregoing are incorporated herein by reference in parts pertinent to encapsulation of stem cells.

Certain embodiments of the current disclosure incorporate stem cells into a polymer, such as a biopolymer or synthetic polymer. Examples of biopolymers include, but are not limited to, fibronectin, fibrin, fibrinogen, thrombin, collagen, and proteoglycans. Other factors, such as the cytokines discussed above, can also be incorporated into the polymer. In other embodiments of the disclosure, stem cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

When referring to cultured vertebrate cells, the term senescence (also replicative senescence or cellular senescence) refers to a property attributable to finite cell cultures; namely, their inability to grow beyond a finite number of population doublings (sometimes referred to as Hayflick's limit). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but rather is measured by the number of cell divisions, or population doublings, the culture has undergone. Thus, cells made quiescent by removing essential growth factors are able to resume growth and division when the growth factors are re-introduced, and thereafter carry out the same number of doublings as equivalent cells grown, continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to programmed cell death (apoptosis), and have been maintained in their nondividing state for as long as three years. These cells are very much alive and metabolically active, but they do not divide. The nondividing state of senescent cells has not yet been found to be reversible by any biological, chemical, or viral agent.

As used herein, the term "Growth Medium" generally refers to a medium sufficient for the culturing of umbilicus-derived cells. In particular, one presently preferred medium for the culturing of the cells of the invention herein comprises Dulbecco's Modified Essential Media (also abbreviated DMEM herein). Particularly preferred is DMEM-low glucose (also DMEM-LG herein) (Invitrogen, Carlsbad, Calif.). The DMEM-low glucose is preferably supplemented with 15% (v/v) fetal bovine serum (e.g. defined fetal bovine serum, Hyclone, Logan Utah), antibiotics/antimycotics (preferably penicillin (100 Units/milliliter), streptomycin (100 milligrams/milliliter), and amphotericin B (0.25 micrograms/milliliter), (Invitrogen, Carlsbad, Calif.)), and 0.001% (v/v) 2-mercaptoethanol (Sigma, St. Louis Mo.). In some cases different growth media are used, or different supplementations are provided, and these are normally indicated in the text as supplementations to Growth Medium.

In some embodiments of the current disclosure, standard growth conditions are utilized. As used herein, the term "standard growth conditions" refers to culturing of cells at 37° C., in a standard atmosphere comprising 5% $CO_2$. Relative humidity is maintained at about 100%. While foregoing the conditions are useful for culturing, it is to be understood that such conditions are capable of being varied by the skilled artisan who will appreciate the options available in the art for culturing cells, for example, varying the temperature, $CO_2$, relative humidity, oxygen, growth medium, and the like.

In some embodiments of the current disclosure, the conditioned media used to treat addiction is generated by using dedifferentiated fibroblasts. In some embodiments, fibroblasts are treated with a variety of dedifferentiated compositions that can endow increased pluripotency. In some embodiments, fibroblasts are treated with cytoplasm from a more undifferentiated cell. Such cells, commonly known as pluripotent stem cells are well known in the art and methods of derivation are published and incorporated by reference. Without limitation, useful pluripotent cells of extraction of cytoplasm include parthenogenic stem cells [9-23], embryonic stem cells [24-25], inducible pluripotent stem cells [26-30], Stimulus-triggered acquisition of pluripotency (STAP) [31], and somatic cell nuclear transfer derived stem cells [32-34]. Extraction of cytoplasmic matter may be performed as described in the art.

In some embodiments of the current disclosure, pluripotent cells are made to enter the interphase stage of cell cycle and are harvested using standard methods and washed by centrifugation at 500×g for 10 minutes in a 10 ml conical tube at 4° C. The supernatant is discarded, and the cell pellet is resuspended in a total volume of 50 ml of cold PBS. The cells are centrifuged at 500×g for 10 minutes at 4° C. This washing step is repeated, and the cell pellet is resuspended in approximately 20 volumes of ice-cold interphase cell lysis buffer (20 mM Hepes, pH 8.2, 5 mM MgCl2, 1 mM DTT, 10 .mu.M aprotinin, 10 .mu.M leupeptin, 10 .mu.M pepstatin A, 10 .mu.M soybean trypsin inhibitor, 100 .mu.M PMSF, and preferably 20 .mu.g/ml cytochalasin B). The cells are sedimented by centrifugation at 800×g for 10 minutes at 4° C. The supernatant is discarded, and the cell pellet is carefully resuspended in no more than one volume of interphase cell lysis buffer. The cells are incubated on ice for one hour to allow swelling of the cells. The cells are lysed by either sonication using a tip sonicator or Dounce homogenization using a glass mortar and pestle. Cell lysis is performed until at least 90% of the cells and nuclei are lysed, which may be assessed using phase contrast microscopy. The sonication time required to lyse at least 90% of the cells and nuclei may vary depending on the type of cell used to prepare the extract. The cell lysate is placed in a 1.5-ml centrifuge tube and centrifuged at 10,000 to 15,000×g for 15 minutes at 4° C. using a table top centrifuge. The tubes are removed from the centrifuge and immediately placed on ice. The supernatant is carefully collected using a 200 μl pipette tip, and the supernatant from several tubes is pooled and placed on ice. This supernatant is the "interphase cytoplasmic" or "IS15" extract. This cell extract may be aliquoted into 20 μl volumes of extract per tube on ice and immediately flash-frozen on liquid nitrogen and stored at −80° C. until use. Alternatively, the cell extract is placed in an ultracentrifuge tube on ice (e.g., fitted for an SW55 Ti rotor; Beckman). If necessary, the tube is overlayed with mineral oil to the top. The extract is centrifuged at 200,000×g for three hours at 4° C. to sediment membrane vesicles contained in the 1515 extract. At the end of centrifugation, the oil is discarded. The supernatant is carefully collected, pooled if necessary, and placed in a cold 1.5 ml tube on ice. This supernatant is referred to as "IS200" or "interphase cytosolic" extract. The extract is aliquoted and frozen as described for the IS15 extract. If desired, the extract can be enriched with additional nuclear factors. For example, nuclei can be purified from cells of the cell type from which the reprogramming extract is derived and lysed by sonication as described above. The nuclear factors are extracted by a 10-60 minute incubation in nuclear buffer containing NaCl or KCl at a concentration of 0.15-800 mM under agitation. The lysate is centrifuged to sediment unextractable components. The supernatant containing the extracted factors of interest is dialyzed to eliminate the NaCl or KCl. The dialyzed nuclear extract is aliquoted and stored frozen. This nuclear extract is added at various concentrations to the whole cell extract described above prior to adding the nuclei for reprogramming.

Some embodiments of the current disclosure comprise an alternative to a cell extract, such as reprogramming media. A reprogramming medium can be formed by adding one or more naturally-occurring or recombinant factors (e.g., nucleic acids or proteins such as T-cell receptors or other signaling surface molecules, DNA methyltransferases, histone deacetylases, histones, nuclear lamins, transcription factors, activators, repressors, growth factors, hormones, or cytokines) to a solution, such as a buffer. Preferably, one or more of the factors are specific for the cell type one wishes the donor cell to become.

In some embodiments, the extract is used for reprogramming of fibroblasts by culture. In one embodiment, fibroblasts grown on coverslips are reversibly permeabilized with the bacterial toxin Streptolysin O, exposed to extracts of pluripotent stem cells and resealed with 2 mM $CaCl_2$, and expanded in culture. In one embodiment, fibroblasts are grown on 16-mm poly-L-lysine-coated coverslips in RPMI1640 to 100,000 cells/coverslip in 12-well plates. Cells are permeabilized in 200 ng/ml streptolysin 0 in $Ca^{+2}$ free Hanks Balanced Salt Solution (Gibco-BRL) for 50 minutes at 37° C. in regular atmosphere. Over 80% of fibroblasts cells are permeabilized under these conditions, as judged by propidium iodide uptake. Streptolysin 0 is aspirated; coverslips overlaid with 80 χl of either pluripotent stem cell extract; and incubated for one hour at 37° C. in $CO_2$ atmosphere. Each extract contained the ATP generating system and 1 mM each of ATP, CTP, GTP and UTP. Extracts from pluripotent stem cells are prepared as described above. To reseal plasma membranes, RPMI1640 containing 2 mM $CaCl_2$ (added from a 1 M stock in $H_2O$) is added to the wells, and the cells are incubated for two hours at 37° C. This procedure resealed about 100% of the permeabilized cells. $Ca^{+2}$ containing RPMI was replaced by RPMI, and the cells are expanded for several weeks. Several descriptions of cytoplasmic transferring have been published and are incorporated by reference [35-37]. Once dedifferentiated fibroblasts are obtained, conditioned media, and or exosomes from said conditioned media are concentrated and used therapeutically by administration into a patient who is addicted. Administration may be performed intranasally, intravenously, orally, and/or subcutaneously.

Formulations, Dosage and Routes of Administration

Embodiments include pharmaceutical, therapeutic compositions, formulations, preparations and related methods for treating opioid addiction comprising fibroblast cells or products derived thereof.

Compositions take the form of a solution, suspension, a film for example, and contain about 10% to about 95% or about 25% to about 70% of cells or products derived thereof. In embodiments, the compositions are administered in any of a number of suitable ways. Compositions may be administered systemically by means such as intravenous and intraarterial, locally, by means such as intrathecally, intraventricularly, or by means of an Ommaya reservoir. Other means including transdermally, rectally, vaginally, sublingually, and intranasally.

Compositions are administered in a manner compatible and in such amount as will be therapeutically effective, tolerable and safe. The quantity administered depends on the subject to be treated. Precise amounts of cells required to be administered depend on the judgment of the practitioner.

In many instances, it may be desirable to have multiple administrations of at most about or at least about 3, 4, 5, 6, 7, 8, 9, 10, or more (or any range derivable therein). The administration may range from one day to multiple week interval of 1, 2, 3, 4, 5, 6, 7, 8, 9, 10 or more weeks (or any range derivable therein). The course of administration may be followed by assessment of symptoms, pain, mood, behavior, or catastrophizing for example.

As used herein a "pharmaceutically acceptable" or "pharmacologically acceptable" compositions The dosage of the pharmaceutical compositions and formulations depends on the type of formulation and varies according to the size and health of the subject. Various combination and dosages are contemplated and are within the scope of the current invention and within the scope of "pharmaceutically acceptable" or "pharmacologically acceptable" compositions, such as, by way of example, any dosage anywhere between 5-100 mg for memantine in combination with the cells or compositions of the current disclosure. The phrase "pharmaceutically acceptable" refers to molecular entities and compositions that do not produce an adverse, allergic or other untoward reaction when administered to an animal or human.

Upon formulation, solutions will be administered in a manner compatible with the dosage formulation and in such amount as is therapeutically or prophylactically effective. The formulations are easily administered in a variety of dosage forms. An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

In certain embodiments, a subject is administered memantine, naloxone, acompatase or other compounds with the fibroblast compositions of the current disclosure, in an amount of about, at least about, or at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 milligrams (mg) or micrograms (mcg) or µg/kg or micrograms/kg/minute or mg/kg/min or micrograms/kg/hour or mg/kg/hour, or any range derivable therein.

A dose may be administered on an as needed basis or every 1, 2, 3, 4, 5, 6, 7, 8, 9, 10, 11, 12, 18, or 24 hours (or any range derivable therein) or 1, 2, 3, 4, 5, 6, 7, 8, 9, or times per day (or any range derivable therein). A dose may be first administered before or after signs of a condition. In some embodiments, the patient is administered a first dose of a regimen 1, 2, 3, 4, 5, 6, 7, 8, 9, 10, 11, 12 hours (or any range derivable therein) or 1, 2, 3, 4, or 5 days after the patient experiences or exhibits signs or symptoms of the condition (or any range derivable therein). The patient may be treated for 1, 2, 3, 4, 5, 6, 7, 8, 9, 10 or more days (or any range derivable therein) or until symptoms of the condition have disappeared or been reduced or after 6, 12, 18, or 24 hours or 1, 2, 3, 4, or 5 days after symptoms have disappeared or been reduced.

In some embodiments, treatments of subjects may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

A patient may be administered a composition or a combination of compounds described herein in an amount that is, is at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg (or any range derivable therein).

A patient may be administered a composition or a combination of compounds described herein in an amount that is, is at least, or is at most about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500 mg/kg/day (or any range derivable therein).

Cell Encapsulation

In some embodiments, the fibroblasts of the current disclosure may be encapsulated. It is contemplated that any of the many methods of cell encapsulation available may be employed. In some embodiments, cells are individually encapsulated. In some embodiments, many cells are encapsulated within the same membrane. In embodiments in which the cells are to be removed following implantation, a relatively large size structure encapsulating many cells, such as within a single membrane, may provide a convenient means for retrieval. A wide variety of materials may be used in various embodiments for microencapsulation of stem cells. Such materials include, for example, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, and polyethersulfone (PES) hollow fibers. Techniques for microencapsulation of cells that may be used for administration of stem cells are known to those of skill in the art and are described, for example, in Chang, P., et al., 1999; Matthew, H. W., et al., 1991; Yanagi, K., et al., 1989; Cal Z. H., et al., 1988; Chang, T. M., 1992 and in U.S. Pat. No. 5,639,275 (which, for example, describes a biocompatible capsule for long-term maintenance of cells that stably express biologically active molecules. Additional methods of encapsulation are in European Patent Publication No. 301,777 and U.S. Pat. Nos. 4,353,888; 4,744,933; 4,749, 620; 4,814,274; 5,084,350; 5,089,272; 5,578,442; 5,639, 275; and 5,676,943. All of the foregoing are incorporated herein by reference in parts pertinent to encapsulation of stem cells. Certain embodiments incorporate stem cells into a polymer, such as a biopolymer or synthetic polymer. Examples of biopolymers include, but are not limited to, fibronectin, fibin, fibrinogen, thrombin, collagen, and proteoglycans. Other factors, such as the cytokines discussed above, can also be incorporated into the polymer. In other embodiments of the invention, stem cells may be incorporated in the interstices of a three-dimensional gel. A large polymer or gel, typically, will be surgically implanted. A polymer or gel that can be formulated in small enough particles or fibers can be administered by other common, more convenient, non-surgical routes.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

REFERENCES

The following references and the publications referred to throughout the specification, to the extent that they provide exemplary procedural or other details supplementary to those set forth herein, are specifically incorporated herein by reference.

1. Seth, P., et al., Overdose Deaths Involving Opioids, Cocaine, and Psychostimulants—United States, 2015-2016. MMWR Morb Mortal Wkly Rep, 2018. 67(12): p. 349-358.
2. Votaw, V. R., et al., Perceived risk of heroin use among nonmedical prescription opioid users. Addict Behav, 2017. 65: p. 218-223.
3. Al-Tayyib, A. A., S. Koester, and P. Riggs, Prescription opioids prior to injection drug use: Comparisons and public health implications. Addict Behav, 2017. 65: p. 224-228.
4. Banerjee, G., et al., Non-medical use of prescription opioids is associated with heroin initiation among US veterans: a prospective cohort study. Addiction, 2016. 111(11): p. 2021-2031.
5. Srivastava, A., M. Kahan, and M. Nader, Primary care management of opioid use disorders: Abstinence, methadone, or buprenorphine-naloxone? Can Fam Physician, 2017. 63(3): p. 200-205.
6. Valenstein-Mah, H., et al., Underutilization of the current clinical capacity to provide buprenorphine treatment for opioid use disorders within the Veterans Health Administration. Subst Abus, 2018: p. 1-3.
7. Ronquest, N. A., et al., Relationship between buprenorphine adherence and relapse, health care utilization and costs in privately and publicly insured patients with opioid use disorder. Subst Abuse Rehabil, 2018. 9: p. 59-78.
8. Leung, L. S., et al., Brain areas that influence general anesthesia. Prog Neurobiol, 2014. 122: p. 24-44.
9. Vrana, K. E., et al., Nonhuman primate parthenogenetic stem cells. Proc Natl Acad Sci USA, 2003. 100 Suppl 1: p. 11911-6.
10. Sanchez-Pernaute, R., et al., Long-term survival of dopamine neurons derived from parthenogenetic primate embryonic stem cells (cyno-1) after transplantation. Stem Cells, 2005. 23(7): p. 914-22.
11. Cibelli, J. B., K. Cunniff, and K. E. Vrana, Embryonic stem cells from parthenotes. Methods Enzymol, 2006. 418: p. 117-35.
12. Revazova, E. S., et al., Patient-specific stem cell lines derived from human parthenogenetic blastocysts. Cloning Stem Cells, 2007. 9(3): p. 432-49.
13. de Fried, E. P., et al., Human parthenogenetic blastocysts derived from noninseminated cryopreserved human oocytes. Fertil Steril, 2008. 89(4): p. 943-7.
14. French, A. J., S. H. Wood, and A. O. Trounson, Human therapeutic cloning (NTSC): applying research from mammalian reproductive cloning. Stem Cell Rev, 2006. 2(4): p. 265-76.
15. Lin, G., et al., A highly homozygous and parthenogenetic human embryonic stem cell line derived from a one-pronuclear oocyte following in vitro fertilization procedure. Cell Res, 2007. 17(12): p. 999-1007.
16. Revazova, E. S., et al., HLA homozygous stem cell lines derived from human parthenogenetic blastocysts. Cloning Stem Cells, 2008. 10(1): p. 11-24.
17. De Sousa, P. A. and I. Wilmut, Human parthenogenetic embryo stem cells: appreciating what you have when you have it. Cell Stem Cell, 2007. 1(3): p. 243-4.
18. Wun, I. C. and R. E. Dittman, Human somatic cell nuclear transfer. Chin J Physiol, 2008. 51(4): p. 208-13.
19. Taupin, P., Parthenogenetically activated human oocytes and parthenogenetic embryonic stem cells: US20100233143. Expert Opin Ther Pat, 2011. 21(8): p. 1281-3.
20. Wei, Q., et al., Derivation of rhesus monkey parthenogenetic embryonic stem cells and its microRNA signature. PLoS One, 2011. 6(9): p. e25052.
21. Yabuuchi, A., H. Rehman, and K. Kim, Histocompatible parthenogenetic embryonic stem cells as a potential source for regenerative medicine. J Mamm Ova Res, 2012. 29(1): p. 17-21.
22. Daughtry, B. and S. Mitalipov, Concise review: parthenote stem cells for regenerative medicine: genetic, epigenetic, and developmental features. Stem Cells Transl Med, 2014. 3(3): p. 290-8.
23. Espejel, S., et al., Brief report: Parthenogenetic embryonic stem cells are an effective cell source for therapeutic liver repopulation. Stem Cells, 2014. 32(7): p. 1983-8.
24. Cervera, R. P. and M. Stojkovic, Human embryonic stem cell derivation and nuclear transfer: impact on regenerative therapeutics and drug discovery. Clin Pharmacol Ther, 2007. 82(3): p. 310-5.
25. De Sousa, P. A., et al., Clinically failed eggs as a source of normal human embryo stem cells. Stem Cell Res, 2009. 2(3): p. 188-97.
26. Takahashi, K. and S. Yamanaka, Induction of pluripotent stem cells from mouse embryonic and adult fibroblast cultures by defined factors. Cell, 2006. 126(4): p. 663-76.
27. Park, I. H., et al., Reprogramming of human somatic cells to pluripotency with defined factors. Nature, 2008. 451(7175): p. 141-6.
28. Chhabra, A., Derivation of Human Induced Pluripotent Stem Cell (iPSC) Lines and Mechanism of Pluripotency: Historical Perspective and Recent Advances. Stem Cell Rev, 2017.
29. Shi, Y., et al., Induced pluripotent stem cell technology: a decade of progress. Nat Rev Drug Discov, 2017. 16(2): p. 115-130.
30. Kele, M., et al., Generation of human iPS cell line CTL07-II from human fibroblasts, under defined and xeno-free conditions. Stem Cell Res, 2016. 17(3): p. 474-478.
31. Obokata, H., et al., Bidirectional developmental potential in reprogrammed cells with acquired pluripotency. Nature, 2014. 505(7485): p. 676-80.
32. Zhou, Q., et al., A comparative approach to somatic cell nuclear transfer in the rhesus monkey. Hum Reprod, 2006. 21(10): p. 2564-71.
33. Hall, V. J., et al., Developmental competence of human in vitro aged oocytes as host cells for nuclear transfer. Hum Reprod, 2007. 22(1): p. 52-62.
34. Sung, L. Y., et al., Efficient derivation of embryonic stem cells from nuclear transfer and parthenogenetic embryos derived from cryopreserved oocytes. Cell Reprogram, 2010. 12(2): p. 203-11.
35. Collas, P. and C. K. Taranger, Epigenetic reprogramming of nuclei using cell extracts. Stem Cell Rev, 2006. 2(4): p. 309-17.

36. Collas, P. and C. K. Taranger, Toward reprogramming cells to pluripotency. Ernst Schering Res Found Workshop, 2006(60): p. 47-67.
37. Collas, P., et al., On the way to reprogramming cells to pluripotency using cell-free extracts. Reprod Biomed Online, 2006. 12(6): p. 762-70.

The invention claimed is:

1. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers,
   wherein said fibroblast cell is generated by a method comprising the step of culturing under suitable conditions a plurality of fibroblasts, obtaining a single cell suspension from said plurality, and extracting from said single cell suspension fibroblast cells expressing markers CD31 and/or CD73, and
   wherein culturing of said fibroblast cells occurs in a conditioned medium.

2. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers,
   wherein said fibroblast cell is generated by a method comprising the step of culturing under suitable conditions a plurality of fibroblasts, obtaining a single cell suspension from said plurality, and extracting from said single cell suspension fibroblast cells expressing markers CD31 and/or CD73, and
   further comprising activating said fibroblast cells by exposure to one or more toll like receptor agonists.

3. The method of claim 2, wherein said toll like receptor is TLR-1.

4. The method of claim 3, wherein said agonist of TLR-1 is Pam3CSK4.

5. The method of claim 2, wherein said toll like receptor is TLR-2.

6. The method of claim 5, wherein said agonist of TLR-2 is HKLM.

7. The method of claim 2, wherein said toll like receptor is TLR-3.

8. The method of claim 7, wherein said agonist of TLR-3 is Poly:IC.

9. The method of claim 2, wherein said toll like receptor is TLR-4.

10. The method of claim 9, wherein an agonist of TLR-4 is LPS, Buprenorphine, Carbamazepine, Fentanyl, Levorphanol, Methadone, Cocaine, Morphine, Oxycodone, Pethidine, Glucuronoxylomannan from Cryptococcus, Morphine-3-glucuronide, lipoteichoic acid, β-defensin 2, small molecular weight hyaluronic acid, fibronectin EDA, snapin, Oxcarbazepine, or tenascin C.

11. The method of claim 2, wherein said toll like receptor is TLR-5.

12. The method of claim 11, wherein said agonist of TLR-5 is flagellin.

13. The method of claim 2, wherein said toll like receptor is TLR-6.

14. The method of claim 13, wherein said agonist of TLR-6 is FSL-1.

15. The method of claim 2, wherein said toll like receptor is TLR-7.

16. The method of claim 15, wherein said agonist of TLR-7 is imiquimod.

17. The method of claim 2, wherein said toll like receptor of TLR-8.

18. The method of claim 14, wherein said agonist of TLR8 is ssRNA40/LyoVec.

19. The method of claim 2, wherein said toll like receptor of TLR-9.

20. The method of claim 19, wherein said agonist of TLR-9 is a CpG oligonucleotide, ODN2006, or Agatolimod.

21. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers, and
   wherein the subject is also administered memantine.

22. The method of claim 21, wherein the subject is also administered 5-100 mg/day or 10-30 mg/day memantine.

23. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers, and
   wherein the subject is also administered one or more analgesics.

24. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers, and
   wherein the subject is also administered Naloxone.

25. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers, and
   wherein the subject is also administered Acamprosate.

26. A method of treating addiction or substance abuse in a subject, the method comprising administering to the subject a composition comprising a fibroblast cell, a plurality thereof and/or a product derived thereof,
   wherein the fibroblast cell is cultured in a growth medium, in a conditioned medium or in a reprogramming medium, and wherein the fibroblast cell expresses CD31 and/or CD73 markers, and
   wherein the fibroblast cell or plurality thereof is encapsulated.

27. The method of claim 26, wherein the fibroblast cell or plurality thereof is encapsulated by a membrane, polymer capsules, alginate-poly-L-lysine-alginate microcapsules, barium poly-L-lysine alginate capsules, barium alginate capsules, polyacrylonitrile/polyvinylchloride (PAN/PVC) hollow fibers, or polyethersulfone (PES) hollow fibers.

28. A method of treating addiction or substance abuse in a subject, the method comprising administering to the subject a composition comprising a fibroblast cell, a plurality thereof and/or a product derived thereof,
    wherein the fibroblast cell is cultured in a growth medium, in a conditioned medium or in a reprogramming medium, and wherein the fibroblast cell expresses CD31 and/or CD73 markers, and
    wherein the product derived thereof comprises a supernatant from a fibroblast cell culture.

29. The method of claim 28, wherein the supernatant from a fibroblast cell culture comprises at least one trophic factor.

30. The method of claim 29, wherein the trophic factor is a hormone, cytokine, extracellular matrix, protein, vesicle, antibody, granules, or a mixture thereof.

31. A method of treating addiction or substance abuse in a subject, the method comprising administering to the subject a composition comprising a fibroblast cell, a plurality thereof and/or a product derived thereof,
    wherein the fibroblast cell is cultured in a growth medium, in a conditioned medium or in a reprogramming medium, and wherein the fibroblast cell expresses CD31 and/or CD73 markers, and
    wherein said fibroblast cell or plurality thereof further express CD45 and/or CD34 markers.

* * * * *